United States Patent [19]
Crowley

[11] Patent Number: 5,630,837
[45] Date of Patent: May 20, 1997

[54] ACOUSTIC ABLATION

[75] Inventor: Robert J. Crowley, Wayland, Mass.

[73] Assignee: Boston Scientific Corporation, Natick, Mass.

[21] Appl. No.: 415,514

[22] Filed: Mar. 31, 1995

Related U.S. Application Data

[63] Continuation-in-part of Ser. No. 86,523, Jul. 1, 1993, abandoned.

[51] Int. Cl.$^6$ .................................................. A61F 7/00
[52] U.S. Cl. ................ 601/2; 128/662.06; 128/660.03
[58] Field of Search .......................... 128/660.03, 662.06; 604/22; 601/2; 606/49; 607/97, 115, 122

[56] References Cited

U.S. PATENT DOCUMENTS

| | | | |
|---|---|---|---|
| 3,938,502 | 2/1976 | Bom | 128/2 |
| 4,757,820 | 7/1988 | Itoh | 128/660.03 |
| 4,936,281 | 6/1990 | Stasz | 128/660.03 |
| 4,951,677 | 8/1990 | Crowley et al. | 128/662.06 |
| 5,000,185 | 3/1991 | Yock | 128/662.03 |
| 5,002,059 | 3/1991 | Crowley et al. | 128/662.06 |
| 5,131,397 | 7/1992 | Crowley | 128/662.06 |
| 5,186,177 | 2/1993 | O'Donnell et al. | 128/662.06 |
| 5,222,501 | 6/1993 | Ideker et al. | 128/660.03 |
| 5,281,215 | 1/1994 | Milder | 606/20 |
| 5,295,484 | 3/1994 | Marcus et al. | 128/660.03 |
| 5,325,860 | 7/1994 | Seward et al. | 128/662.06 |
| 5,331,966 | 7/1994 | Bennett et al. | 128/696 |
| 5,345,940 | 9/1994 | Seward et al. | 128/660.03 |
| 5,368,035 | 11/1994 | Hamm et al. | 128/662.06 |
| 5,368,557 | 11/1994 | Nita et al. | 604/22 |
| 5,372,138 | 12/1994 | Crowley et al. | 128/662.06 |
| 5,375,601 | 12/1994 | Nicholas et al. | 128/662.06 |
| 5,385,148 | 1/1995 | Lesh et al. | 128/660.03 X |
| 5,409,000 | 4/1995 | Imran | 128/600.03 X |
| 5,454,373 | 10/1995 | Koger et al. | 128/742 |

FOREIGN PATENT DOCUMENTS

| | | |
|---|---|---|
| WO94/07446 | 4/1994 | WIPO. |
| WO95/01751 | 1/1995 | WIPO. |

OTHER PUBLICATIONS

James D. Koger et al., "Medical Acoustic Imaging," USSN 08/278 079, filed Jul. 20, 1994.

Crowley et al., International Journal of Cardiac Imaging 6, "Ultrasound guided therapeutic catheters: recent developments and clinical results", pp. 145–156, 1991.

Crowley, Robert, SPIE Catheter–Based Sensing and Imaging Technology, "Ultrasound Catheter Imaging", vol. 1068 pp. 160–165, 1989.

Crowley et al., International Journal of Cardiac Imaging 4, "Optimized ultrasound imaging catheters for use in the vascular system", pp. 145–151, 1989.

Avitall et al., University of Wisconsin–Milwaukee Clinical Campus, "The Physics and Engineering of Transcatheter Cardiac Tissue Ablation".

Bom et al., 1973 Ultrasonics symposium Proceedings, "Two Multi–Element Systems for Real Time Cross–Sectional Analysis of the Heart", pp. 1–3, 1973.

(List continued on next page.)

Primary Examiner—Francis Jaworski
Attorney, Agent, or Firm—Lyon & Lyon

[57] ABSTRACT

The invention features a catheter system and a method for tissue ablation. A catheter body of extended length is constructed for delivery to locations within a body of a living being and for connection to a power source. An array of acoustic transducers are constructed for receiving power from the power source and for generating acoustic energy, in response to power received from the power source. The acoustic energy generated by the acoustic transducers is sufficient for ablation of tissue. A mechanism independently controls one or more of the ablation transducers to produce a desired acoustic energy pattern for ablating tissue at a select location spaced from the catheter system. The acoustic transducers have an annular configuration designed for generating acoustic energy that radiates in a radial pattern surrounding the circumference of the catheter body.

76 Claims, 13 Drawing Sheets

OTHER PUBLICATIONS

Bom et al., Cardiovascular Imaging and Image Processing, "The Technology fo Miniature Acoustic Element Array", vol. 72, pp. 11–15, 1975.

Bom et al., Ultrasonics, "An ultrasonic intracardiac scanner", Mar. 1972.

Bom et al., SPIE Catheter–Based Sensing and Imaging Technology, "Early and present examples of intraluminal ultrasonic echography", vol. 1068, pp. 146–150, 1989.

Bom et al., Proceedings of the Ninth Annual Conference of the IEEE Engineering in Medicine and Biology Society "Sensing Methods for Selective Recanalization By Spark Erosion", vol. 1 of 4, 1987.

Bom et al., Ultrasound in Med. & Biol., "Intra–Arterial Ultrasonic Imaging for Recanalization By Spark Erosion", vol. 14, No. 4, pp. 257–261, 1988.

Bom et al., "Early and recent intraluminal ultrasound devices", pp. 79–88.

Slager et al., American College of Cardiology, "Vaporizaion of Atherosclerotic Plaques By Spark Erosion" vol. 5, Jun. 1985.

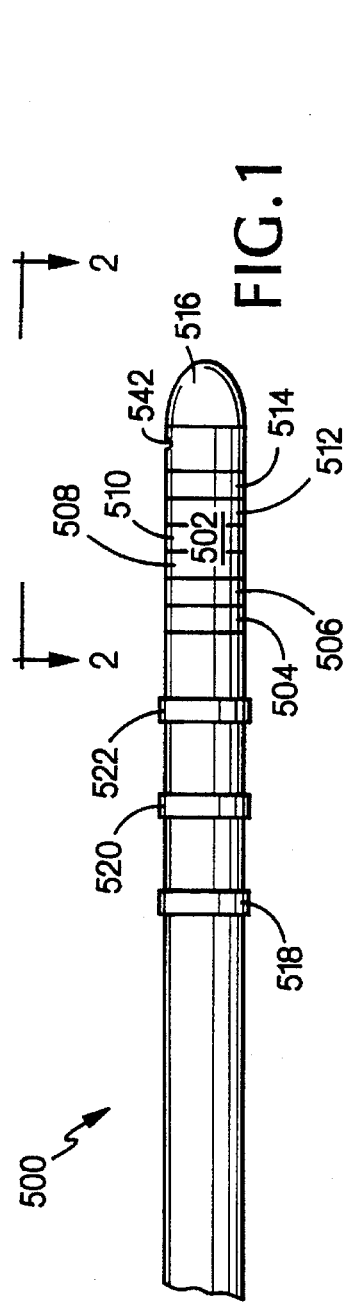
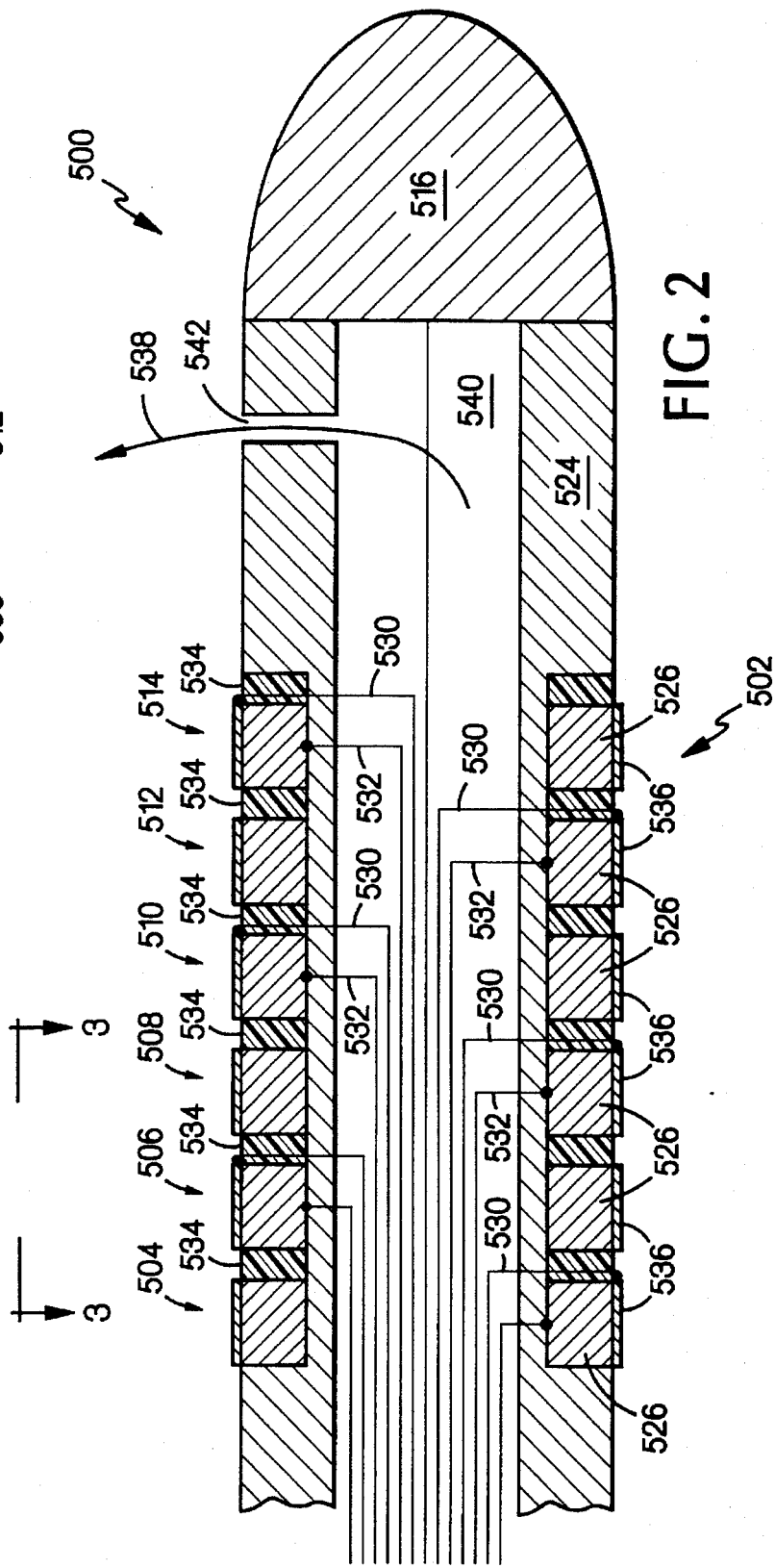
FIG. 1
FIG. 2

ACOUSTIC ABLATION

BACKGROUND

This is a continuation-in-part of U.S. patent application Ser. No. 08/086,523, filed on Jul. 1, 1993, and now abandoned assigned to the same assignee as this application, the entire disclosure of which is hereby incorporated herein by reference.

FIELD OF THE INVENTION

This invention relates to ablation of tissue with acoustic energy.

Currently there are a number of medical and surgical treatments for cardiac arrhythmias, including, drugs, cryoablation, surgery, pacemakers, radio frequency (RF) ablation, and laser ablation. Several of these procedures thread a catheter, with one or more ablation elements near its end, through the vascular system into the heart. For example, Marcus et al., U.S. Pat. No. 5,295,484, discloses a cardiac ablation catheter having an array of half-cylinder shaped ablation transducers. These catheters may also include one or more electrodes for mapping signal transmission through the cardiac tissue to locate discrete areas of the heart responsible for the arrhythmia.

SUMMARY OF THE INVENTION

In one aspect, the invention features a catheter system that generates acoustic energy for tissue ablation that radiates in a radial pattern surrounding the circumference of the catheter. The catheter body is of extended length and is constructed for delivery to locations within a body of a living being and for connection to a power source. An array of acoustic transducers are constructed for receiving power from the power source and for generating acoustic energy, in response to power received from the power source, sufficient for ablation of tissue. A mechanism independently controls one or more of the ablation transducers to produce a desired acoustic energy pattern for ablating tissue at a select location spaced from the catheter. The acoustic transducers have an annular configuration designed for generating acoustic energy that radiates in a radial pattern surrounding the circumference of the catheter body.

Because the transducers are annular in shape, they maximize the available catheter surface area and fit easily within catheter sheaths. Additionally, the radial pattern of acoustic energy generated by the annular configuration of the transducers allows the physician to create 360° (i.e., ring-shaped) lesions without rotation of the catheter and provides a passageway (i.e., lumen 540) through which cooling fluid can be passed. Moreover, such annular transducers can be inexpensive, easy to manufacture, and mechanically strong.

In another aspect, the invention features a catheter system for tissue ablation having an acoustic ablation device and a lumen in communication with a fluid port, where the fluid port is constructed to cause fluid to pass between the lumen and a space external to the catheter body. The lumen is constructed to cause fluid to pass in a longitudinal direction relative to the catheter body and in the vicinity of the acoustic ablation device to cool the acoustic ablation device.

Causing fluid to pass in a longitudinal direction in the vicinity of the acoustic ablation device efficiently cools the acoustic ablation device. A large amount of power may be applied to the ablation transducers to cause the ablation transducers to generate acoustic energy sufficient to ablate tissue. As the transducers generate acoustic energy, they also generate heat. Efficient cooling can prevent heat damage to the transducers and the catheter system and permit larger amounts of power to be applied to the transducers.

In another aspect, the invention features a catheter system for tissue ablation having an acoustic ablation device and a sonolucent standoff balloon for positioning the acoustic ablation device in proximity to tissue to be ablated. The acoustic ablation device is positioned to ablate the tissue by passage of acoustic energy through the balloon.

Using the sonolucent standoff balloon to position the acoustic ablation device allows precise movement of the acoustic device to create precise lesions. Further, the stability of the balloon permits the acoustic ablation device to be located and relocated through predetermined movement of the catheter body to particular positions within the body of the living being. Moreover, sliding the catheter body up and down within the balloon reduces the potential for tissue or valve damage that may occur if the catheter is moved up and down within the body of the living being without a balloon.

In another aspect, the invention features a catheter system for tissue ablation having an acoustic energy redirection device positioned in the vicinity of the acoustic ablation device that is constructed for redirecting acoustic energy produced by the acoustic ablation device toward tissue to be ablated.

Redirecting the acoustic energy increases and focuses the acoustic energy in tissue toward which the energy is redirected. Consequently, all of the acoustic energy produced by the acoustic device may be utilized to ablate a specific tissue portion, and energy which would otherwise travel away from the tissue to be ablated may not be wasted.

Implementations may include the following features. The redirection device may be a reflecting shield positioned about a portion of the acoustic ablation device. The catheter system may also include a rotation mechanism coupled to the catheter for rotating the catheter about its axis.

In another aspect, the invention features a catheter system for tissue ablation having an array of acoustic transducers and a mechanism for selectively controlling each of the ablation transducers to produce a desired acoustic energy pattern for ablating tissue at a select location spaced from the catheter. The mechanism includes a power applicator configured for providing power to one or more of the transducers independently of other ones of the transducers, and a phase shifter configured for shifting the phase of the power provided to one or more of the transducers independently of other ones of the transducers.

The use of a mechanism having a power applicator and a phase shifter enables acoustic energy transmitted from the transducers to be manipulated to create specific acoustic energy radiation patterns. These specific patterns can be used to provide different shaped lesions, including linear lesions and circular lesions, without moving the catheter system.

Additional advantages and features are apparent from the following.

DESCRIPTION

FIG. 1 is a side view of the distal end of an acoustic ablation electrophysiology catheter having a tip electrode, an acoustic ablation transducer array, and ring electrodes.

FIG. 2 is an enlarged cross-sectional side view along line 2—2 in FIG. 1.

STRUCTURE

Figure 3:
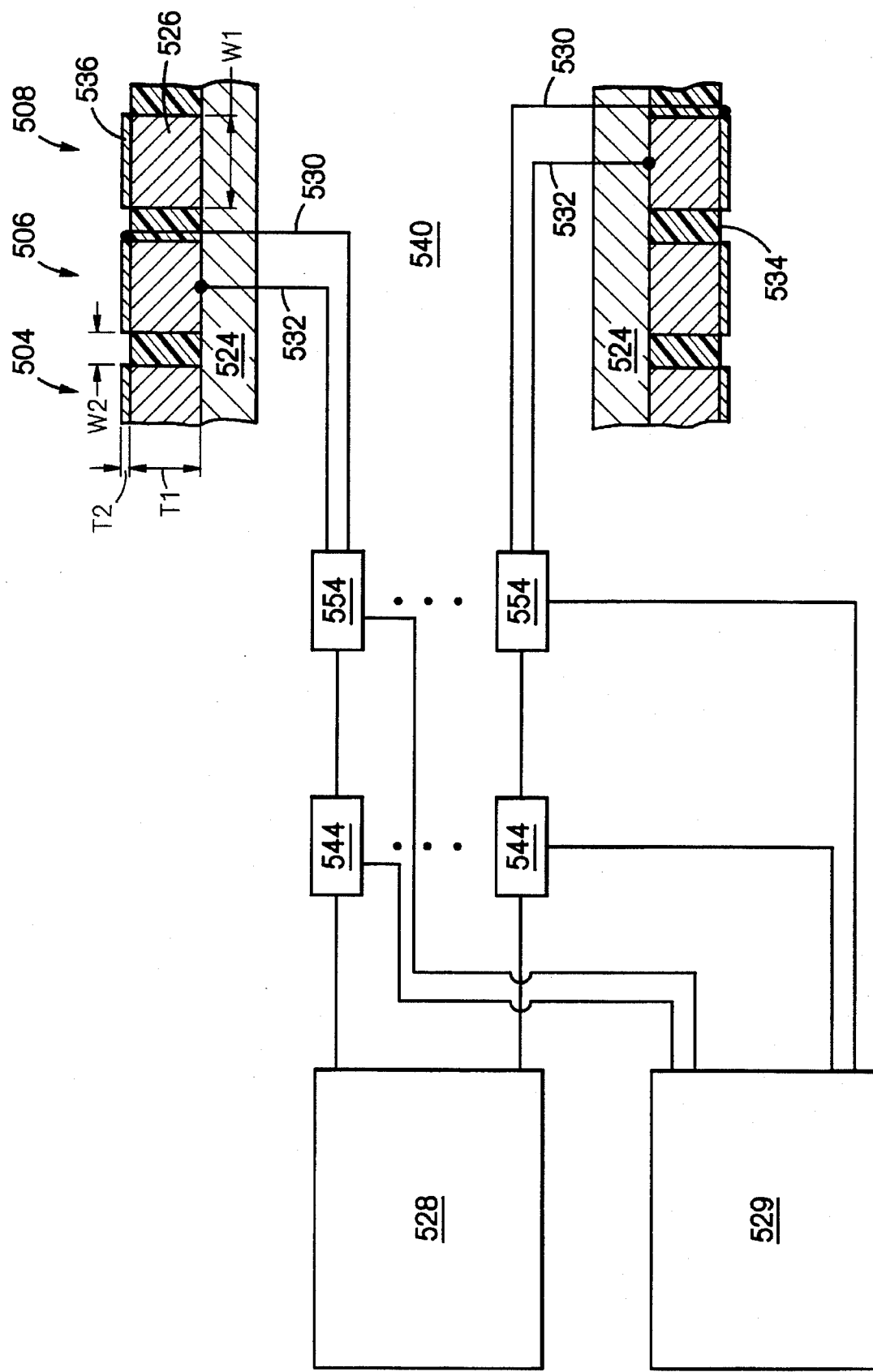
FIG. 3 is a schematic illustrating the connection between control electronics and the transducer array in FIG. 2.

Referring to FIG. 1, an acoustic ablation electrophysiology catheter 500 includes an array 502 of annular acoustic elements 504-514 for tissue ablation. Catheter 500 also includes tip electrode 516 for radio frequency (RF) electric current tissue ablation and ring electrodes 518-522 for tissue mapping. Referring to FIG. 2, cooling fluid, indicated by arrow 538, is passed through lumen 540 in catheter shaft 524 and out fluid port 542.

Referring to FIGS. 2 and 3, each acoustic ablation element 504-514 includes a metal-coated transducer ring 526. Acoustic energy is transmitted to the surrounding blood and tissue through a conductive face matching layer 536 that has an acoustic impedance substantially similar to the acoustic impedance of blood. Acoustic insulation 534 is positioned between adjacent transducer rings 526 to improve acoustic wave directivity by electrically and acoustically insulating transducer rings 526 from each other. The rings are embedded in the wall of the catheter to provide a low profile and so that they generate acoustic energy substantially only in radial directions with respect to the catheter axis.

Catheters are generally cylindrical. Hence, annular transducers maximize the available catheter surface area and fit easily within catheter sheaths. Additionally, the annular configuration of the transducers allows the physician to create 360° (i.e., ring-shaped) lesions without rotation of the catheter and provides a passageway (i.e., lumen 540) through which cooling fluid can be passed.

In the exemplary embodiment described above, the annular configuration is a full cylinder, but in alternative embodiments the annular configuration may be somewhat less than a full cylinder, provided, however, that the acoustic energy generated by the transducers forms a radial pattern surrounding the circumference of the catheter body.

Transducer rings 526 are made from piezoelectric materials such as lead metaniobates or lead-ziconate-titinates (e.g., PZT5a, manufactured by Vernitron, Corp.), formed into a ring by drilling, turing, and/or grinding). These annular transducers are inexpensive, easy to manufacture, and strong. For acoustic ablation, transducer rings 526 are robust, having a width, W1, of about 0.010–0.100 inches, and a thickness, T1, of about 0.010–0.100 inches. The beam angle (indicating beam width) produced by the transducers is typically 20° or more (measured from the origin to −3 dB). Matching layers 536 have a thickness, T2, of about 0.010 inches and cover the exterior surface of the transducer rings. Matching layers 536 are made from silver-filled epoxy (available from Emerson and Cummings, Corp.). Acoustic insulation 534 has a width, W2, of about 0.001–0.010 inches and is made from high-strength epoxy, (available from Devcon, Corp.). The rings are held to the catheter by a thin layer of the acoustic insulating epoxy. Alternatively, the rings can be embedded in the catheter polymer, e.g., nylon or polyethylene. The transducers are driven by a continuous sine wave from an ultrasound generator, generating radio frequencies between approximately 1–30 MHz at average ablation power levels of about 1 to 100 Watts.

Typically, acoustic imaging transducer arrays are driven in pulse echo mode (i.e., short acoustic pulses) from an ultrasound generator at an average imaging power level of less than 1 Watt. The beam angle produced by the imaging transducers is typically less than 3°. The short pulse, narrow beam acoustic energy pattern provides high lateral and axial resolution. Images are built from reflections received from a sweep of the area to be imaged using the known angular position of the transducers and the range (distance) of the return reflections.

Referring particularly to FIG. 3, each transducer ring 526 is electrically coupled to a power source 528 through an outer lead 530 connected to the outer surface of the transducer 526 and an inner lead 532 connected to the inner surface of the transducer 526. Leads 530, 532 are covered with an insulating layer (not shown). Power is changed by varying the gain of the amplifiers. The greater the power, the greater the amplitude of the dipole pattern generated by the transducers. High power over an extended period of time, however, can cause excessive tissue ablation and damage the acoustic ablation transducer array.

Switches 544 and delay lines 554 connect each set of leads 530, 532 to generator 528. Switches 544 regulate whether power will or will not be applied to corresponding transducers. Delay lines 554 regulate the phase of the acoustic energy waveforms produced by corresponding transducers 526 by delaying the application of power from generator 528 to corresponding transducers. A user may manually adjust the settings of switches 544 and delay lines 554 or a controller 529 can be used to adjust the settings.

Once acoustic ablation electrophysiology catheter 500 is positioned, some, all, or none of the transducers 526 are activated through switches 544 and the phases of some, all, or none of the transducers are delayed through delay lines 554 to provide a radiation pattern directed at a specific portion of tissue to be ablated. Additionally, the phases of the waveforms generated by transducers 526 can be shifted, e.g., by 180°, when switches 544 are used to reverse the electrical connections between generator 528 and leads 530, 532. By applying power to different combinations of transducers 526 and then shifting the phases of the waveforms generated by those transducers, different radiation patterns are produced.

A natural focusing effect results when the wavelength of the acoustic energy transmitted by each transducer is shorter than the radiating surface (i.e., transducer surface). Hence, aside from changing the shape of the radiation patterns, the depth of the maximas (i.e., focal points) of the acoustic energy radiation patterns can be changed by changing the phase and frequency applied to the transducer rings. Typically, the higher the frequency, the further the maxima is away from the catheter. The control of arrays to form desired patterns is discussed in *Acoustic Wave Device Imaging & Analog Signal Processing*, by Gordon S. Kino pp.227–271 (1987 Prentice-Hall Publishing).

Figure 4:
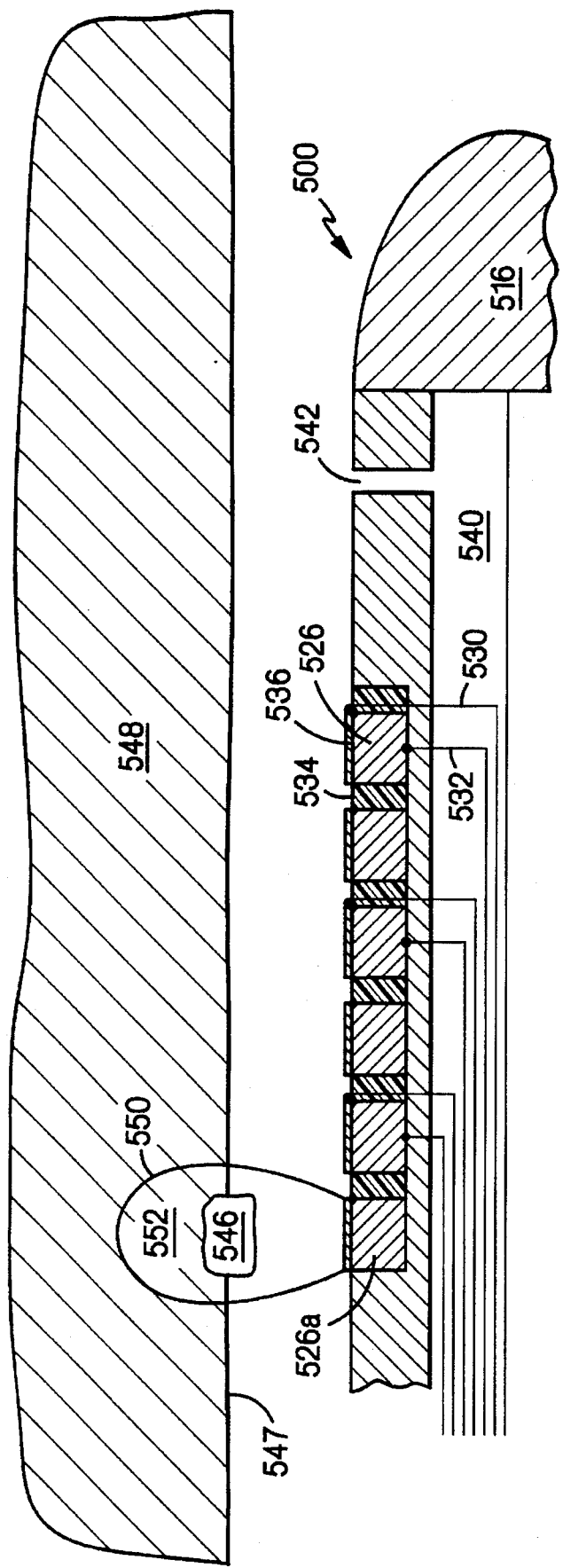
FIG. 4 is a cross-sectional side view of the distal end of an acoustic ablation electrophysiology catheter illustrating an acoustic energy radiation pattern imposed on tissue.

Referring to FIG. 4, discrete tissue portions adjacent the array can be ablated without moving the catheter. For example, to ablate a portion 546 of tissue 548, power is applied to the nearest transducer 526a through its corresponding switch 544 (not shown). When activated, transducer 526a generates acoustic radiation pattern 550. Tissue 548 in the area 552 of acoustic radiation pattern 550 is heated. Only at the maxima within area 552, however, is the heat sufficient to ablate the tissue. Generally, the phase and frequency applied to transducer 526 determines where within area 552 the maxima is located. Hence, to ablate tissue portion 546, a frequency is chosen to locate the maxima at portion 546.

Figure 5:
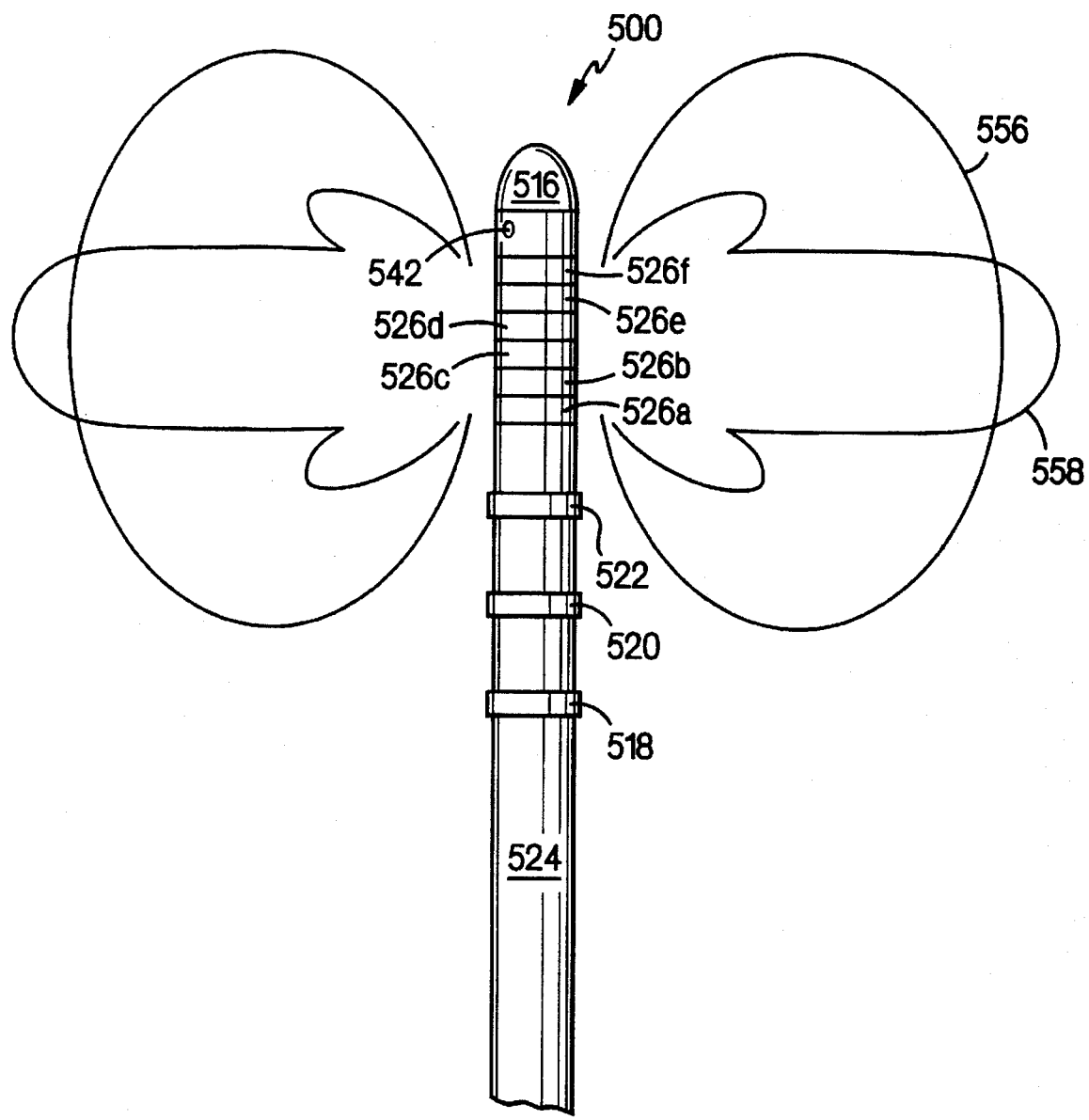
FIG. 5 is a side view of the distal end of an acoustic ablation electrophysiology catheter illustrating other acoustic energy radiation patterns.

Referring to FIG. 5, power can be applied to multiple transducers to generate acoustic energy waveforms sufficient to ablate a specific portion of tissue at a discrete location and depth. For example, a wide pattern 556 is a reference pattern (i.e., common dipole pattern) and results when all of the transducers 526 are in phase (e.g., no delay or an equal delay to each transducer). Shifting (i.e., delaying) the phases of the waveforms of the most proximal and most distal transducers (e.g., 526a and 526f) by several degrees produces elongated (i.e., compressed) pattern 558. Applying power to particular transducers and shifting the phases of the waveforms of those transducers can also produce multiple lobed acoustic energy patterns (not shown).

Figure 6:
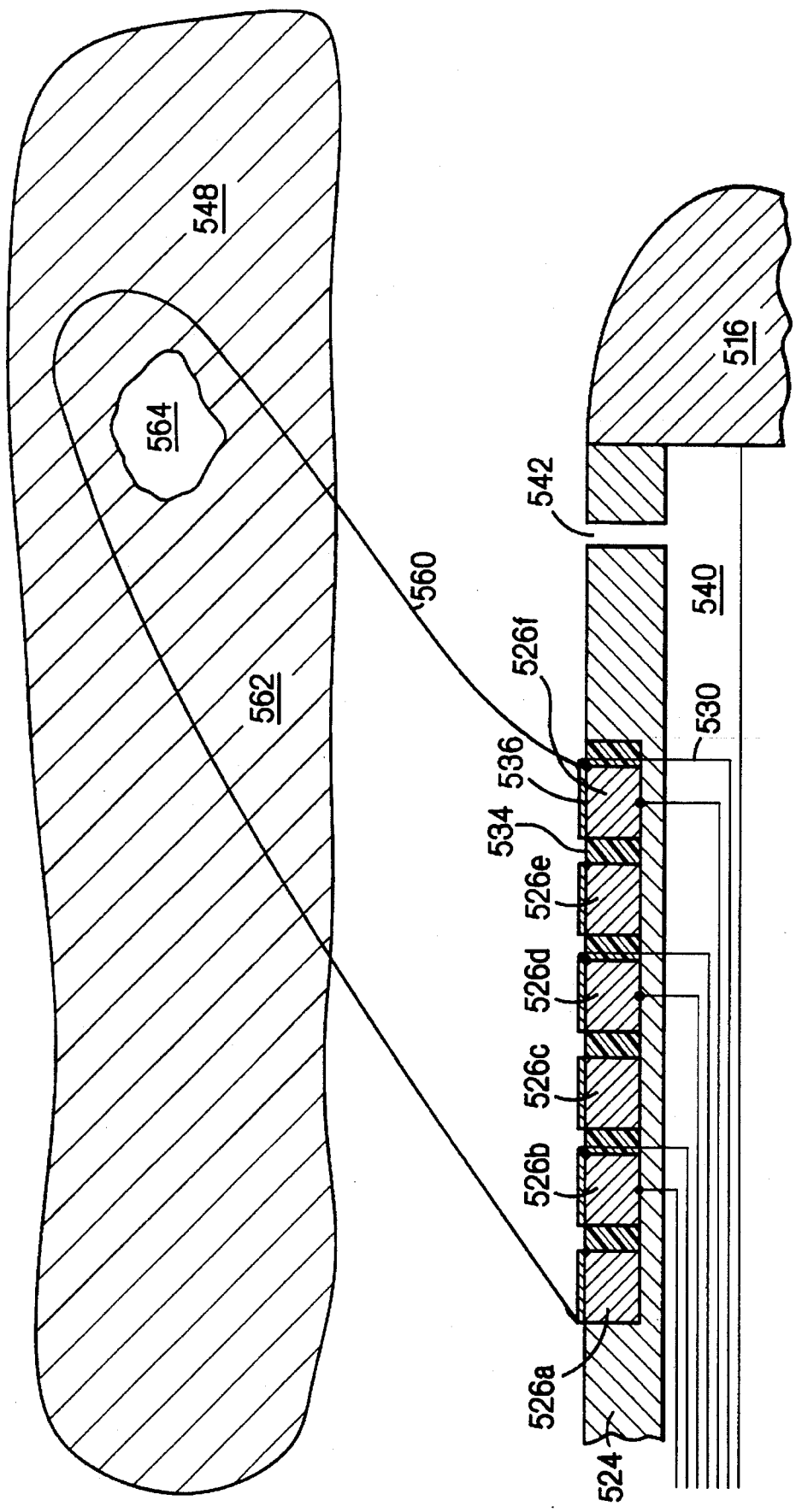
FIG. 6 is a cross-sectional side-view of the distal end of an acoustic ablation electrophysiology catheter illustrating another radiation pattern imposed on tissue.

Referring to FIG. 6, shifting the phases of the waveforms of the distal transducers (e.g., 526e and 526f) by several degrees produces radiation pattern 560 which is located axially beyond the array. Again, although all of tissue 548 in the area 562 is within radiation pattern 560, the frequency is chosen to locate the maxima point of ablation at tissue portion 564.

Use

Figure 7:
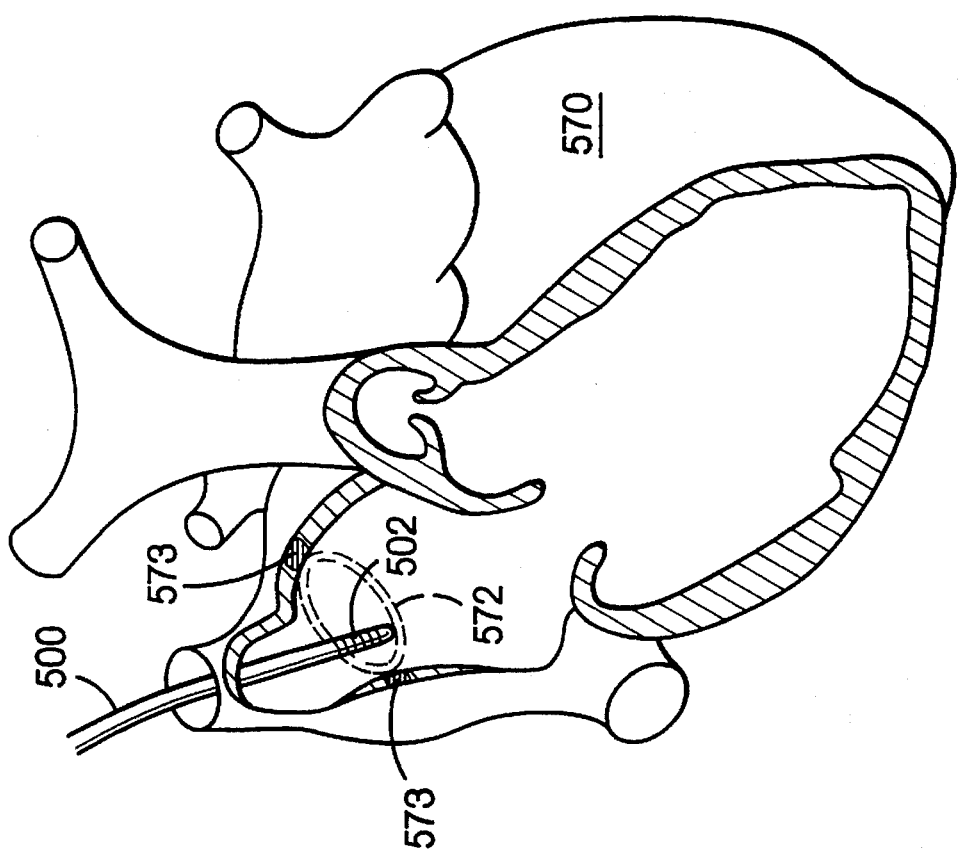
FIG. 7 is a schematic of an acoustic ablation electrophysiology catheter in use in the atrium of the heart.

Referring to FIG. 7, for treatment of atrial fibrillation, catheter 500 is inserted in the atrium of a heart 570. Long, narrow, slice-like shallow lesions are often required for the treatment of atrial fibrillation. Hence, as described above with respect to FIG. 5, transducers of acoustic array 502 are activated, and the waveforms of those transducers are manipulated to generate a disk-like radiation pattern 572 to ablate a long, narrow shallow region 573 of the cardiac tissue around the catheter without moving the catheter or directly contacting the tissue.

Figure 8:
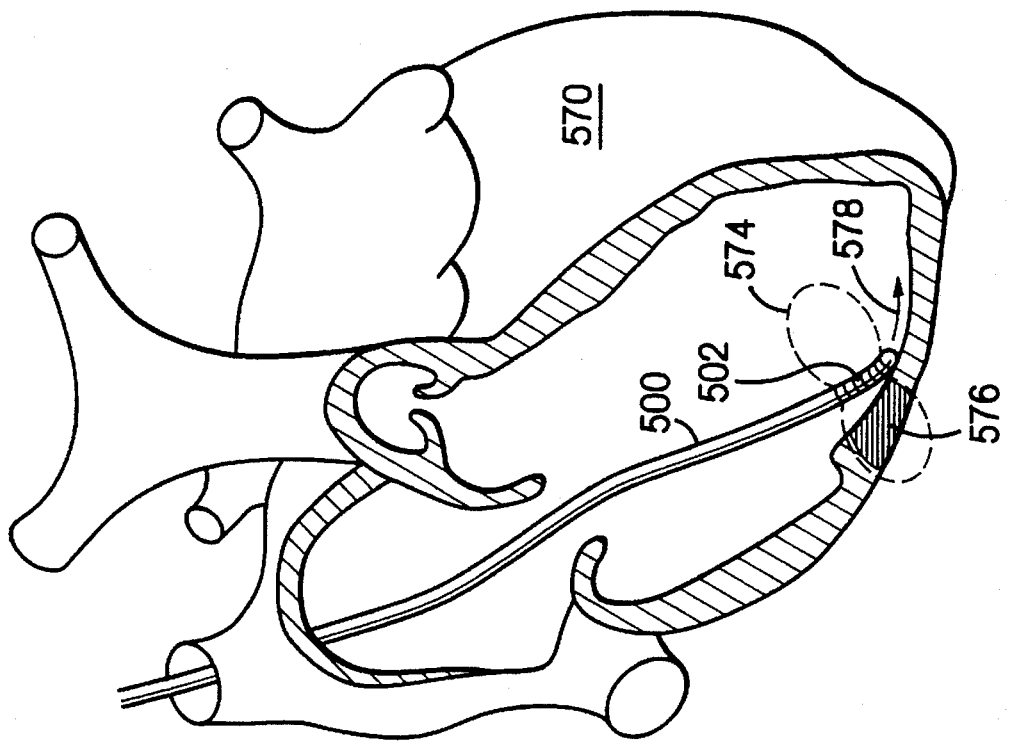
FIG. 8 is a schematic of an acoustic ablation electrophysiology catheter in use in the ventricle of the heart.

Referring to FIG. 8, for the treatment of Ventricular Tachycardia, catheter 500 is inserted in the right ventricle of a human heart 570. Ventricular Tachycardia is seated in the relatively thick myocardium of the ventricles and treatment requires a deep, narrow lesion. Thus, transducers of acoustic array 502 are controlled to produce waveforms that generate a slightly compressed radiation pattern 574 to ablate a deep, narrow region 576 of the cardiac tissue. To create a wider region of ablation, the transducers are activated to create a wave form that gradually moves the ablation zone without moving the catheter. Alternatively, catheter 500 is moved along the direction (e.g., arrow 578) of the desired treatment.

Other Embodiments

Transducers 526 of acoustic ablation array 502 may be connected only to switches 544 or only to delay lines 554. Additionally, delay lines 554 can have fixed or variable delay periods. Continuously variable settings, for selecting any desired acoustic energy radiation pattern, are provided by attaching transducers 526 to switches 544 and to delay lines 554 having variable delay periods. A fixed radiation pattern is provided by attaching transducers 526 only to delay lines 554 having fixed delay periods, while a limited number of predetermined radiation patterns is provided by attaching transducers 526 to switches 544 and delay lines 554 having fixed delay periods.

Figure 9:
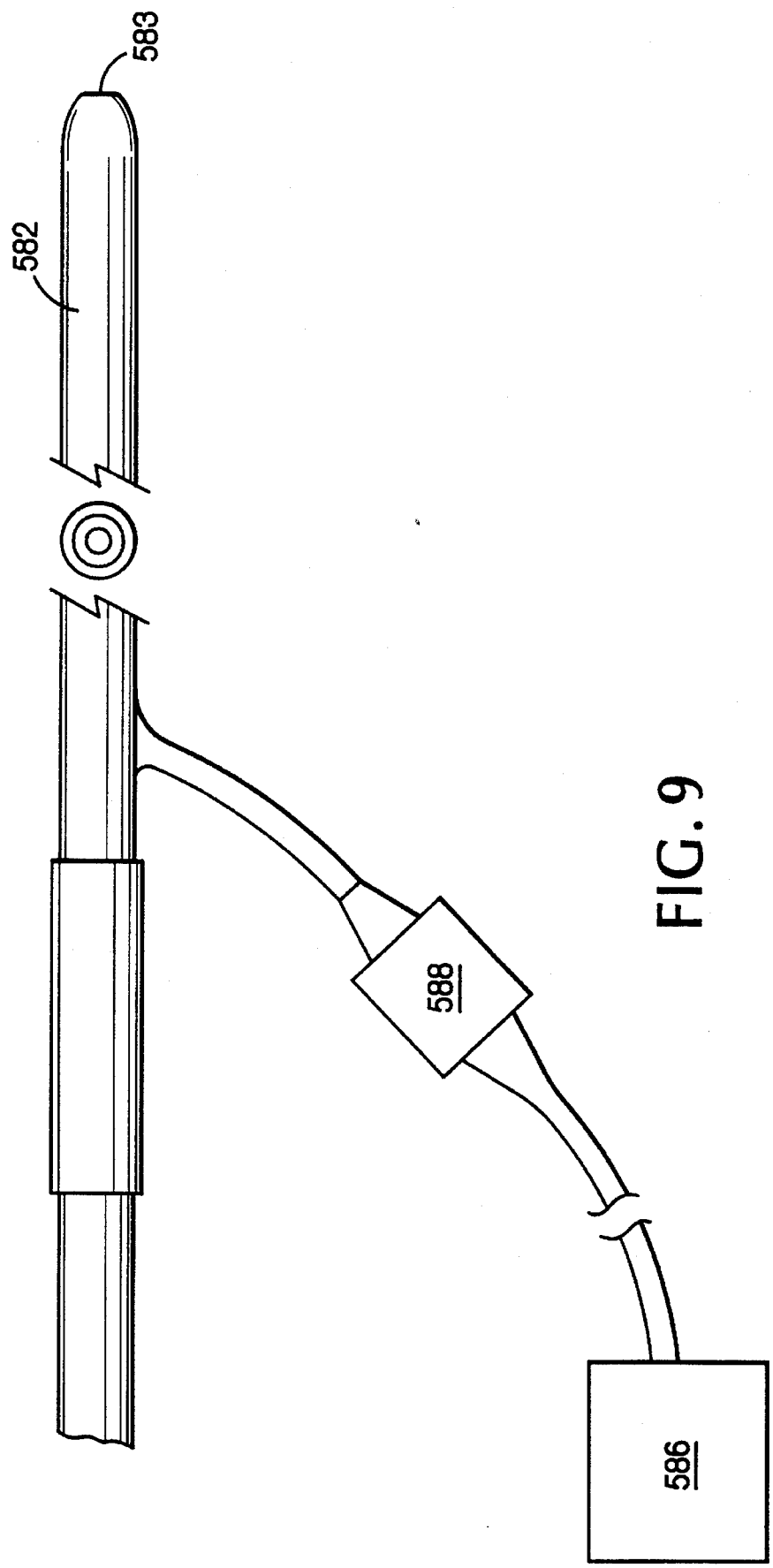
FIG. 9 is a side view of an assembly for receiving an acoustic ablation catheter, including a catheter sheath, a fluid pump, and a regulator.

Referring to FIG. 9, a sheath 582 may be used with a catheter 600 (not shown). Sheath 582 is first inserted into a patient's heart, and moved to a stable location, for example, across a heart valve or within the coronary sinus. Acoustic ablation electrophysiology catheter 600 is then inserted within sheath 582 and, under the guidance of X-ray, positioned near tissue to be ablated. Regulator 586 and fluid pump 588 are used to circulate cooling fluid (not shown) within sheath 582 and out outlet port 583 to cool the transducers.

Alternatively, cooling fluid is circulated through lumen 540 (shown in FIG. 2) in catheter shaft 524, through arrow 538, fluid port 542 and proximally within sheath 582. Passing cooling fluid, in a longitudinal direction relative to the catheter, both through lumen 540 and sheath 582 efficiently cools the transducers by removing heat from both an inner surface (adjacent cooling fluid in lumen 540) and an outer surface (adjacent cooling fluid in sheath 582). Because a portion of the heat generated by the transducers is removed by fluid in lumen 540, the fluid in sheath 582 need not remove all the heat and, as a result, less fluid is required and the size of sheath 582 may be reduced.

Figure 10:
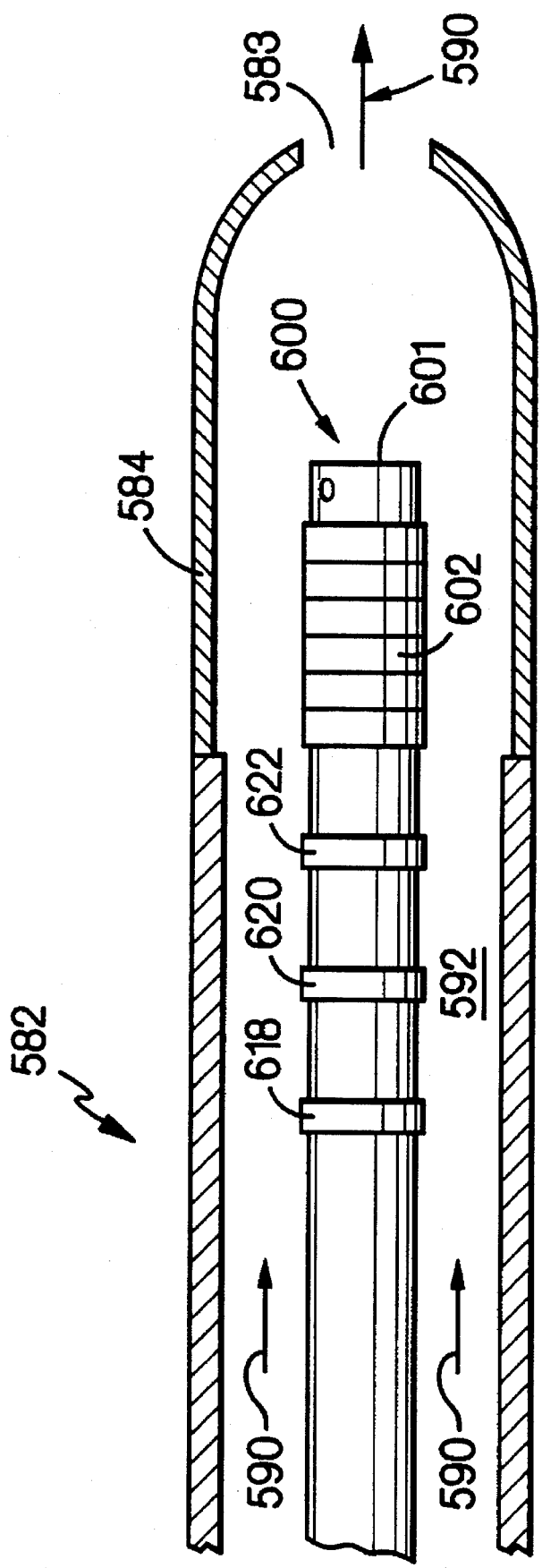
FIG. 10 is a cross-sectional side view including an acoustic ablation electrophysiology assembly including a sheath with an end-opening.

Referring to FIG. 10, sheath 582 may be fully sonolucent or may have a portion 584 of sonolucent material. A sonolucent material such as polyethelyne has good acoustic transmissiveness and allows acoustic radiation energy from acoustic array 602 to pass through and ablate tissue, as discussed above. Catheter 600 may be slid up and down sheath 582 while acoustic array 602 is activated.

The stability of the placement of sheath 582 allows precise movement of array 602 to create precise lesions. Further, the stability of sheath 582 permits array 602 to be located and relocated through predetermined movement of catheter 600 to particular positions within the patient. Moreover, sliding catheter 600 up and down within sheath 582 reduces the potential for tissue or valve damage that may occur if the catheter is moved up and down within the patient without a sheath, and catheter tip 601 can be blunt (i.e., tip 601 need not be rounded).

Cooling fluid such as saline, indicated by arrows 590, can be circulated through catheter shaft lumen 592 and outlet port 583 to remove heat generated by acoustic array 602.

Catheter 600 may also be extended through outlet port 583 to allow ring electrodes 618–622 to be activated.

Figure 11:
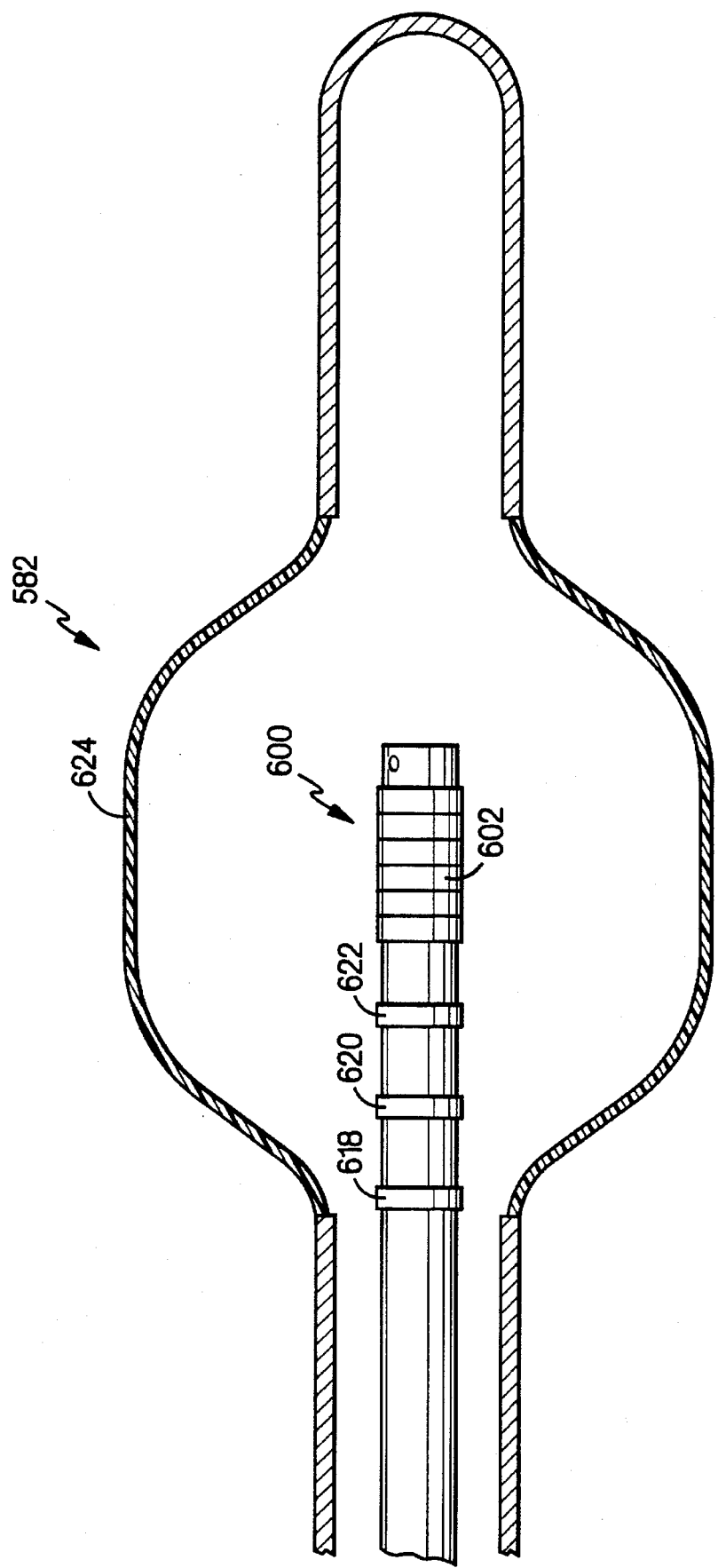
FIG. 11 is a cross-sectional side view of an acoustic ablation electrophysiology assembly including a catheter sheath having a balloon and an acoustic ablation electrophysiology catheter having an acoustic ablation transducer array and ring electrodes.

Referring to FIG. 11, sheath 582 includes a sonolucent standoff balloon 624. Balloon 624 is used to further position and stabilize sheath 582 within, for example, a patient's heart. Again, catheter 600 can be slid up and down within sheath 582 with the above-discussed advantages and fluid pump 586 and regulator 588 can be used to circulate sonolucent cooling fluid through a catheter lumen and sheath 582.

Figure 12:
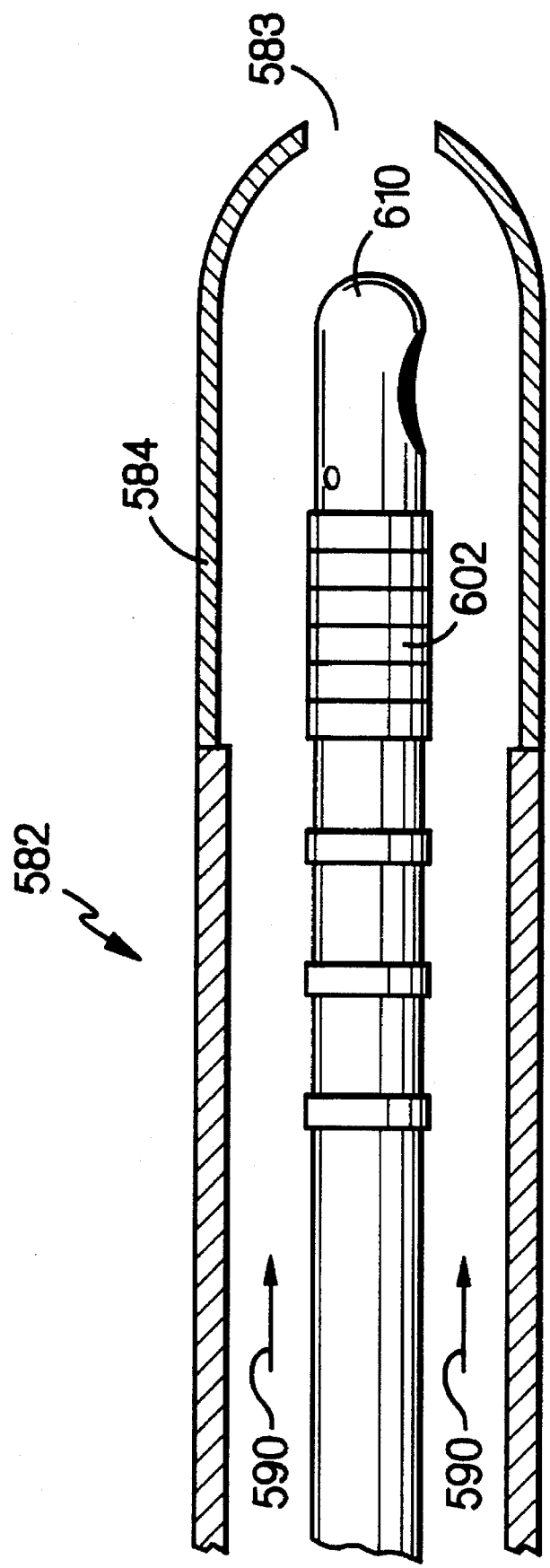
FIG. 12 is a cross-sectional side view of an acoustic ablation electrophysiology assembly including a catheter sheath and an acoustic ablation electrophysiology catheter having an acoustic ablation transducer array, ring electrodes, and an acoustic imaging transducer.

Referring to FIG. 12, catheter 600 includes an acoustic imaging transducer 610. Details of such an imaging transducer are found in U.S. patent application Ser. No. 08/086,523, filed on Jul. 1, 1993, and entitled, "CATHETERS FOR IMAGING, SENSING ELECTRICAL POTENTIALS, AND ABLATING TISSUE." Imaging transducer 610 is used to image, for example, a patient's heart, and position catheter 600 within sheath 582. Catheter 600 including acoustic imaging transducer 610 may be used with or without sheath 582.

Figure 13:
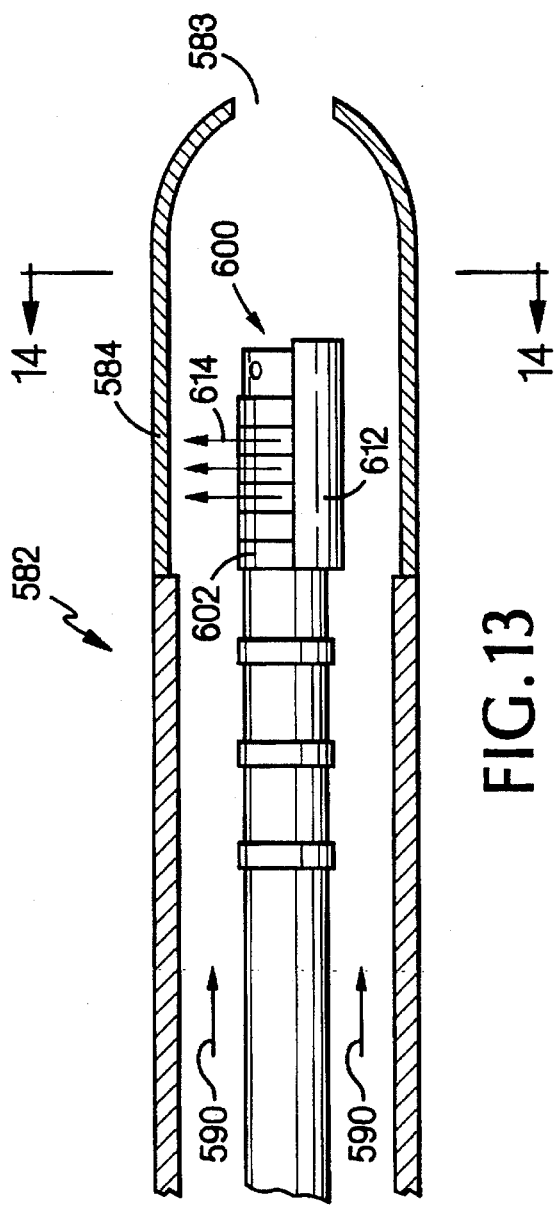
FIG. 13 is a cross-sectional side view of an acoustic ablation electrophysiology assembly including a catheter sheath and an acoustic ablation electrophysiology catheter having ring electrodes, an acoustic ablation transducer array, and a reflecting shield.
Figure 14:
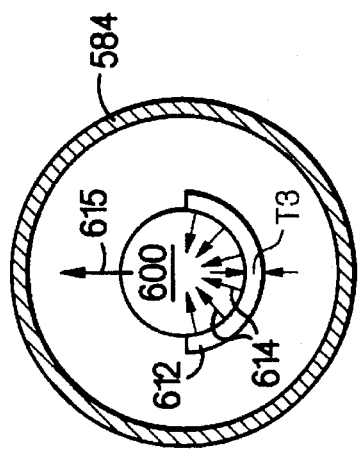
FIG. 14 is a cross-sectional end view along line 14—14 in FIG. 13.

Referring to FIGS. 13 and 14, catheter 600 includes an acoustic reflecting shield 612. Acoustic reflecting shield 612 radially reflects and directs acoustic energy generated by acoustic array 602 and directed at shield 612 in a direction indicated by arrows 614. The energy in the direction of reflection (arrows 614) is increased and focused in relation to the shape of the shield. As one example, the shield can extend about 180° (FIG. 14) around the axis of the array and focus the acoustic energy in a direction indicated by arrow 615. Consequently, all of the acoustic energy produced by acoustic array 602 will be utilized to ablate a specific tissue portion, and energy which would otherwise travel away from the tissue to be ablated will not be wasted.

Acoustic reflecting shield 612 may be stainless steel approximately 0.002–0.005 inches in thickness, T3, and attached to acoustic array 602 with epoxy. Catheter 600 may include a rotation mechanism (not shown) to allow the acoustic energy to be directed at specific locations. Catheter 600, including acoustic reflector 612, may be used with or without sheath 582.

Figure 15:
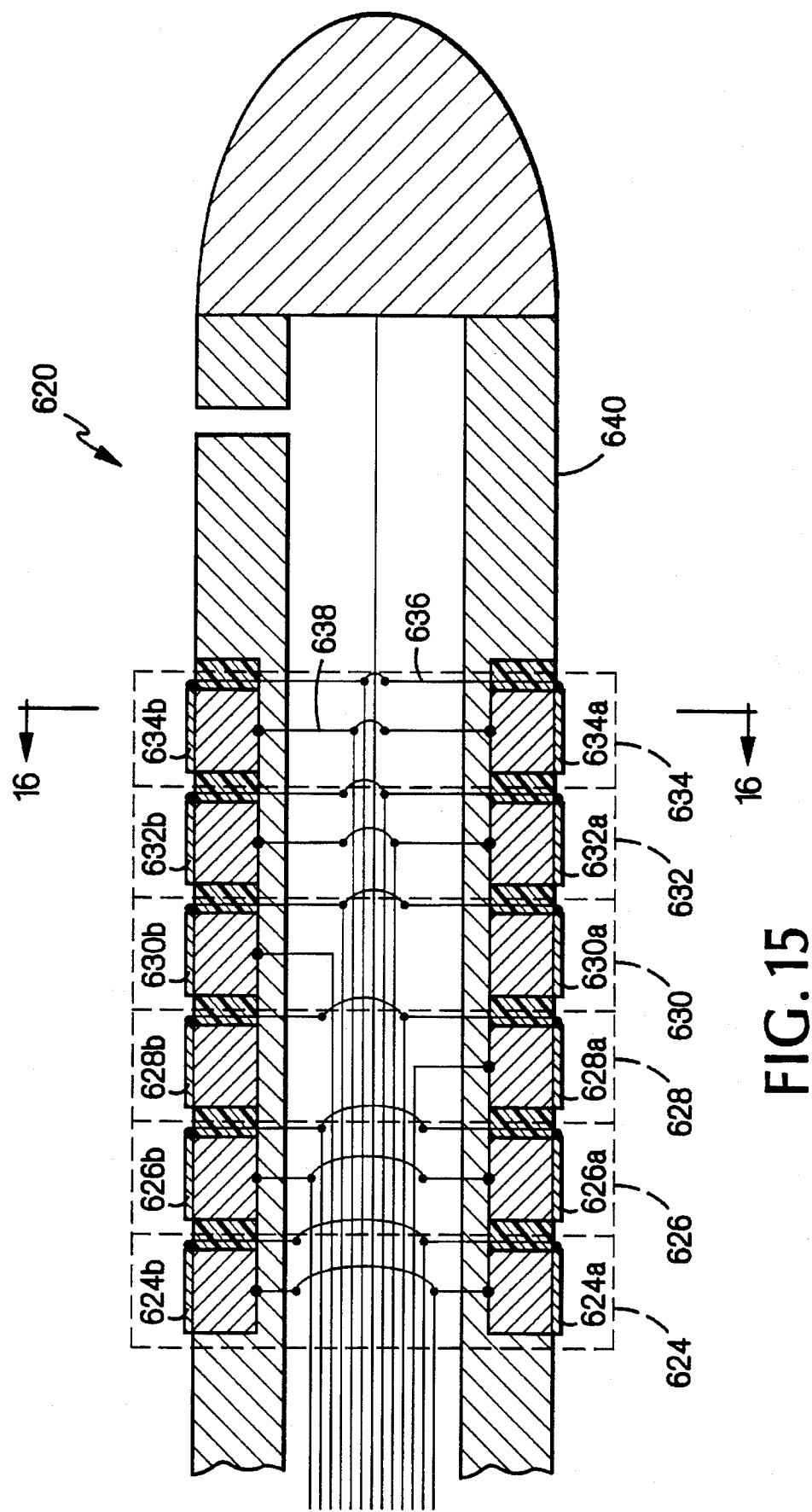
FIG. 15 is a cross-sectional side view of the distal end of an acoustic ablation electrophysiology catheter having a tip electrode, an acoustic ablation transducer array, and ring electrodes.
Figure 16:
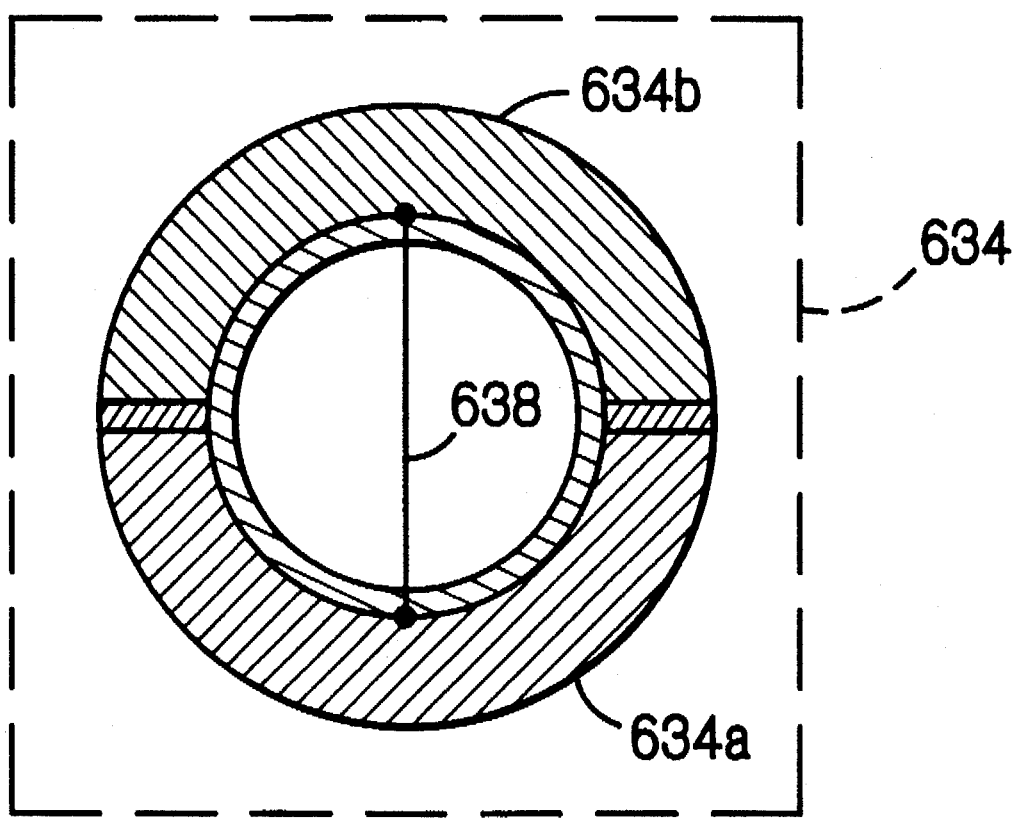
FIG. 16 is a cross-sectional end view along line 16—16 in FIG. 15.

Referring to FIGS. 15 and 16, an acoustic ablation electrophysiology catheter 620 includes an array 622 of acoustic elements 624–634. Each acoustic element 624–634 includes two half-cylinder acoustic transducers: 624a, 624b; 626a, 626b; 628a, 628b; 630a, 630b; 632a, 632b; 634a, 634b. The half-cylinder acoustic transducers of each acoustic element are coupled to a power source (not shown) through an outer lead 636 connected to the outer surfaces of each transducer and an inner lead 638 connected to the inner surfaces of each transducer. Each pair of half-cylinder acoustic transducers provides an acoustic element having an annular configuration and each element generates acoustic energy in a radial pattern surrounding the circumference of the catheter body.

Because the acoustic elements consist of pairs of half-cylinder transducers, array 622 has good flexibility, which permits good articulation of catheter body 640. Additionally, it is easy to connect inner lead 638 to the inner surface of each half-cylinder transducer, and the pairs of half-cylinder transducers are easy to assemble around a central core (i.e., catheter body 640).

Further embodiments are within the following claims.

What is claimed is:

1. A catheter system for tissue ablation, comprising:

a catheter body of extended length constructed for delivery to locations within a body of a living being, said catheter body being adapted for connection to a power source, an array of acoustic transducers disposed along the length of said catheter body and constructed for receiving power from said power source and for generating acoustic energy, in response to said received power, sufficient for ablation of tissue, and a mechanism for controlling one or more of said ablation transducers independently of other ones of said transducers to produce a desired acoustic energy pattern for ablating tissue at a select location spaced from said catheter, at least one of said acoustic transducers having an annular configuration designed for generating acoustic energy that radiates in a radial pattern surrounding the circumference of said catheter body.

2. The catheter system of claim 1, wherein each of said acoustic transducers is a full cylinder having said annular configuration.

3. The catheter system of claim 1, wherein each of said acoustic transducers is a half cylinder and wherein said transducers are arranged in pairs having said annular configuration.

4. The catheter system of claim 1, wherein said annular configuration comprises a full cylinder.

5. The catheter system of claim 1, wherein said controlling mechanism controls said transducers individually.

6. The catheter system of claim 1, wherein the array is a plurality of annular acoustic transducers.

7. The catheter system of claim 1, wherein the mechanism includes a controller.

8. The catheter system of claim 1, wherein the mechanism includes a series of switches, including a switch coupling one or more of said ablation transducers to the power source.

9. The catheter system of claim 1, wherein the mechanism includes a phase controller for selectively varying the phase of said power driving said transducers.

10. The catheter system of claim 9, wherein the mechanism further includes delay lines connecting the ablation transducers to said power source.

11. The catheter system of claim 1 wherein said mechanism includes a frequency control for varying the frequency of the power driving said transducers.

12. The catheter system of claim 1, further comprising:

insulation, positioned between adjacent transducers of the array of acoustic ablation transducers, to electrically and acoustically insulate adjacent transducers from each other.

13. The catheter system of claim 1 wherein said ablation transducers are embedded in the wall of said catheter body.

14. The catheter system of claim 1 including a lumenal space in heat transfer communication with said transducer array for providing a passage for a flow of cooling fluid to cool said transducers.

15. The catheter system of claim 1, wherein adjacent ablation transducers are spaced by a distance of about 0.001 to 0.12 inches.

16. The catheter system of claim 1, wherein said transducers have a beam angle from about 22° to about 122°.

17. The catheter system of claim 1, wherein said transducers are constructed for generating acoustic energy at power levels in the range of about 1 to 102 db.

18. The catheter system of claim 1, further comprising:

an array of matching layers corresponding to and coupled to the array of annular acoustic transducers.

19. The catheter system of claim 1 further comprising:

an acoustic energy redirection device positioned in the vicinity of said acoustic ablation transducer array and configured for directing acoustic energy produced by said acoustic ablation transducer array toward tissue to be ablated.

20. The catheter system of claim 19, wherein said redirection device is a reflecting shield positioned about a portion of said array.

21. The catheter system of claim 20, further comprising:
a rotation mechanism coupled to the catheter body for rotating the catheter body about its axis.

22. The catheter system of claim 1, further comprising:
a sheath for surrounding the catheter body, a portion of the sheath being sonolucent.

23. The catheter system of claim 22, wherein the catheter body includes a catheter lumenal space in heat communication with said transducers and a fluid port in communication with said catheter lumenal space, said catheter body is disposed within said sheath and said sheath further includes a sheath lumenal space for circulating cooling fluid through the sheath lumenal space, the fluid port, and the catheter lumenal space to cool said transducers.

24. The catheter system of claim 22, wherein said catheter body is disposed within said sheath and said sheath further includes a lumenal space in heat communication with said transducers and an outlet port in communication with said lumenal space for circulating cooling fluid through the sheath and the outlet port to cool the ablation transducers.

25. The catheter system of claims 22, wherein said catheter body is disposed within said sheath and said sheath includes an end opening through which said catheter body can be extended.

26. The catheter system of claim 22, wherein the sheath further includes a sonolucent standoff balloon.

27. The catheter system of claim 1, further including an acoustic imaging transducer.

28. The catheter system of claim 1 further including a radio frequency ablation electrode.

29. The catheter system of claim 1 further including mapping electrodes.

30. A catheter system for tissue ablation, comprising:
a catheter body of extended length constructed for delivery to locations within a body of a living being, said catheter body being adapted for connection to a power source,
an acoustic ablation device constructed for receiving power from said power source and for generating acoustic energy, in response to said received power, sufficient for ablation of tissue,
a flexible sheath of extended length constructed for delivery to locations within a body of a living being and constructed to receive said catheter body, said sheath being at least partially sonolucent,
a lumen within said catheter body, and
a fluid port in communication with said lumen and said sheath,
said fluid port being constructed to cause fluid to pass between said lumen and a space external to said catheter body and within said sheath,
said lumen and said sheath being constructed to cause fluid to pass in a longitudinal direction relative to said catheter body and in the vicinity of said acoustic ablation device to cool said acoustic ablation device.

31. The catheter system of claim 30, wherein said acoustic ablation device includes
a radiating outer surface, and
an inner surface.

32. The catheter system of claim 31, wherein said lumen causes fluid to pass in the vicinity of said inner surface.

33. The catheter system of claim 31, where said acoustic ablation device includes
an array of annular acoustic transducers.

34. A catheter system for tissue ablation, comprising:
a catheter body of extended length constructed for delivery to locations within a body of a living being, said catheter body being adapted for connection to a power source,
an acoustic ablation device constructed for receiving power from said power source and for generating acoustic energy, in response to said received power, sufficient for ablation of tissue, and
a sonolucent standoff balloon for positioning said acoustic ablation device in proximity to tissue to be ablated, said acoustic ablation device being positioned to ablate said tissue by passage of acoustic energy through said balloon.

35. A catheter system for tissue ablation, comprising:
a catheter body of extended length constructed for delivery to locations within a body of a living being, said catheter body being adapted for connection to a power source,
an acoustic ablation device constructed for receiving power from said power source and for generating acoustic energy, in response to said received power, sufficient for ablation of tissue, and
an acoustic energy redirection device positioned in the vicinity of said acoustic ablation device and constructed for redirecting a portion of acoustic energy produced by said acoustic ablation device in a direction of another portion of said acoustic energy produced by said acoustic ablation device toward tissue to be ablated.

36. The catheter system of claim 35, further comprising:
a rotation mechanism coupled to the catheter body for rotating the catheter body about its axis.

37. A catheter system for tissue ablation, comprising:
a catheter body of extended length constructed for delivery to locations within a body of a living being, said catheter body being adapted for connection to a power source,
a linear array of annular acoustic transducers disposed along the length of said catheter body and constructed for receiving power from said power source and for generating acoustic energy, in response to said received power, sufficient for ablation of tissue, and
a mechanism for selectively controlling one or more of said ablation transducers to produce a desired acoustic energy pattern for ablating tissue at a select location spaced from said catheter body, said mechanism including:
a power applicator configured for providing power to one or more of said transducers, and
a phase shifter configured for shifting the phase of said power provided to one or more of said transducers independently of other ones of said transducers.

38. The catheter system of claim 37, wherein said mechanism further includes a controller constructed to control said power applicator and said phase shifter.

39. The catheter system of claim 37, wherein said power applicator includes
a series of switches, including a switch coupling one or more of said ablation transducers to the power source.

40. The catheter system of claim 37, wherein said phase shifter includes
a phase controller for selectively varying the phase of said power provided to one or more of said transducers by said power applicator.

41. The catheter system of claim 40, wherein said phase shifter further includes
delay lines connecting one or more of said transducers to said power source.

42. The catheter system of claim 37, wherein said mechanism further includes
a frequency control device for varying the frequency of said power provided to one or more of said transducers by said power applicator.

43. A method for selective acoustic ablation of tissue within the body of a living being, comprising
providing a catheter system for acoustic ablation of tissue, said catheter system comprising:
a catheter body of extended length constructed for delivery to locations within a body of a living being, said catheter body being adapted for connection to a power source,
an array of acoustic transducers disposed along the length of said catheter body and constructed for receiving power from said power source and for generating acoustic energy, in response to said received power, sufficient for ablation of tissue, and
a mechanism for controlling one or more of said ablation transducers independently of other ones of said transducers to produce a desired acoustic energy pattern for ablating tissue at a select location spaced from said catheter body,
at least one of said acoustic transducers having an annular configuration designed for generating acoustic energy that radiates in a radial pattern surrounding the circumference of said catheter body, threading said catheter body into said body of said living being such that the transducer array is located in proximity to tissue to be ablated, and
controlling at least one of said ablation transducers to provide a desired energy pattern for ablation of tissue at a select location separated from said catheter body.

44. The method of claim 43, wherein controlling said transducers provides different shaped lesions.

45. The method of claim 44, wherein the different shaped lesions include a linear lesion.

46. The method of claim 43, wherein controlling said transducers ablates different discrete portions of tissue without moving said catheter body.

47. The method of claim 43, wherein controlling includes providing power selectively to the ablation transducers.

48. The method of claim 43, wherein controlling further includes controlling the phase of power applied to the ablation transducers.

49. The method of claim 43, wherein controlling includes controlling the frequency of power applied to the ablation transducers.

50. The method of claim 43 wherein controlling includes controlling said transducers in said array to ablate select discrete tissue locations radially adjacent select transducers in said array by providing power only to said select transducers and choosing a frequency to locate the maxima at the select discrete tissue locations.

51. The method of claim 43, wherein controlling includes controlling said transducers in said array to ablate a select discrete tissue area by controlling the phase of said transducers in a manner that acoustic energy from multiple transducers causes ablation in said area.

52. The method of claim 51, wherein said area has a width along the device axis that is shorter than said array.

53. The method of claim 51, wherein said area is axially beyond said transducer array.

54. The method of claim 43, wherein controlling includes controlling said transducers to ablate tissue in a ring-like pattern around said catheter body.

55. The method of claim 54, further comprising
delivering said catheter body into an atrium of a heart of said body of said living being for treating fibrillation.

56. The method of claim 43, wherein said catheter system includes mapping electrodes and said method further includes mapping a heart within said body of said living being to determine a location for said ablation.

57. The method of claim 43, further comprising:
flowing cooling fluid through a catheter lumenal space in heat communication with the transducer array to cool the transducer array.

58. The method of claim 43, further comprising, before the step of threading:
inserting the catheter body into a sheath have a sonolucent portion.

59. The method of claim 58, further comprising:
flowing cooling fluid through a sheath lumenal space in said sheath in heat communication with the transducers to cool the transducers.

60. The method of claim 59, wherein the step of flowing includes flowing cooling fluid through an outlet port in communication with said sheath lumenal space.

61. The method of claim 59, wherein the step of flowing includes flowing cooling fluid through a fluid port in communication with a catheter lumenal space and said sheath lumenal space.

62. A method for tissue ablation comprising:
providing a catheter system for acoustic ablation as described in claim 1,
positioning said catheter system with an imaging device within a heart of said body of said living being such that the transducer array is located in proximity to cardiac tissue to be ablated,
controlling one or more of said ablation transducers to provide a therapeutic energy pattern for ablation of tissue at a select location, and
withdrawing the catheter system from the body of the living being.

63. A method for tissue ablation, comprising:
positioning a flexible sheath of extended length within a body of a living being, said sheath being at least partially sonolucent,
inserting a catheter system having a catheter body of extended length within said sheath, said catheter body being adapted for connection to a power source,
providing power from said power source to an acoustic ablation device constructed for receiving power,
generating acoustic energy with said acoustic ablation device, in response to said received power, said acoustic energy being sufficient for ablation of tissue, and
passing fluid through a lumen within said catheter body and through a fluid port in communication with said lumen and said sheath, said fluid port being constructed to cause the fluid to pass between said lumen and a space external to said catheter body and within said sheath, and said lumen and said sheath being constructed to cause the fluid to pass in a longitudinal direction relative to said catheter body and in the vicinity of said acoustic ablation device to cool said acoustic ablation device.

64. The method of claim 63, wherein generating acoustic energy includes radiating acoustic energy from an outer surface of said acoustic ablation device.

65. The method of claim 64, wherein radiating acoustic energy includes radiation of acoustic energy in a radial pattern surrounding the circumference of said catheter body.

66. The method of claim 63, wherein passing fluid through said lumen causes fluid to pass in the vicinity of an inner surface of said acoustic ablation device.

67. A method for tissue ablation, comprising:

positioning a catheter body of extended length within a body of a living being, said catheter body being adapted for connection to a power source, providing power to an acoustic ablation device constructed for receiving power from said power source, generating acoustic energy with said acoustic ablation device, in response to said received power, said acoustic energy being sufficient for ablation of tissue, placing a sonolucent standoff balloon within the body of the living being, inserting said catheter body within said balloon such that said acoustic ablation device is positioned in proximity to tissue to be ablated, and ablating said tissue by passage of acoustic energy through said balloon.

68. A method for tissue ablation, comprising:

positioning a catheter body of extended length within a body of a living being, said catheter body being adapted for connection to a power source, providing power to an acoustic ablation device constructed for receiving power from said power source, generating acoustic energy with said acoustic ablation device, in response to said received power, said acoustic energy being sufficient for ablation of tissue, and redirecting a portion of said acoustic energy in a direction of another portion of said acoustic energy toward tissue to be ablated, with an acoustic energy redirection device positioned in the vicinity of said acoustic ablation device.

69. The method of claim 68, wherein redirecting said acoustic energy includes reflecting said acoustic energy.

70. The method of claim 68, wherein redirecting includes rotating said catheter body about its axis.

71. A method for tissue ablation, comprising:

positioning a catheter body of extended length within a body of a living being, said catheter body being adapted for connection to a power source, providing power to a linear array of annular acoustic transducers disposed along the length of said catheter body and constructed for receiving power from said power source, generating acoustic energy with said array of acoustic transducers, in response to said received power, said acoustic energy being sufficient for ablation of tissue, and ablating tissue at a select location spaced from said catheter body by selectively controlling one or more of said ablation transducers independently of others of said ablation transducers to produce a desired acoustic energy pattern, including providing said power to one or more of said transducers independently of other ones of said transducers, and shifting the phase of said power provided to one or more of said transducers independently of other ones of said transducers.

72. The method of claim 71, wherein generating acoustic energy includes radiating acoustic energy in a radial pattern surrounding the circumference of said catheter body.

73. The method of claim 71, wherein providing said power includes switching said power on and off to one or more of said ablation transducers.

74. The method of claim 73, wherein varying the phase further includes delaying the application of said power to one or more of said transducers.

75. The method of claim 71, wherein shifting the phase includes varying the phase of said power provided to one or more of said transducers.

76. The method of claim 71, wherein ablating tissue further includes varying the frequency of said power provided to one or more of said transducers.

* * * * *

UNITED STATES PATENT AND TRADEMARK OFFICE
CERTIFICATE OF CORRECTION

PATENT NO. : 5,630,837
DATED : May 20, 1997
INVENTOR(S) : Robert J. CROWLEY

It is certified that error appears in the above-indentified patent and that said Letters Patent is hereby corrected as shown below:

Column 6, line 50, change "polyethelyne" to --polyethylene--.

Column 10, line 3, change "where" to --wherein--.

Column 12, line 12, after "electrodes" add --,--.

Column 12, line 21, change "have" to --having--.

Signed and Sealed this

Eleventh Day of November, 1997

Attest:

BRUCE LEHMAN

Attesting Officer Commissioner of Patents and Trademarks

UNITED STATES PATENT AND TRADEMARK OFFICE
CERTIFICATE OF CORRECTION

PATENT NO. : 5,630,837
DATED : May 20, 1997
INVENTOR(S) : Robert J. CROWLEY

It is certified that error appears in the above-indentified patent and that said Letters Patent is hereby corrected as shown below:

Column 4, line 17, change "turing" to --turning--.
Column 9, line 27, change "claims" to --claim--.

Signed and Sealed this

Tenth Day of February, 1998

Attest:

BRUCE LEHMAN

*Attesting Officer*     *Commissioner of Patents and Trademarks*